US009663752B2

(12) United States Patent
Gebauer et al.

(10) Patent No.: US 9,663,752 B2
(45) Date of Patent: May 30, 2017

(54) COLLAPSIBLE BAG WITH FLEXIBLE VORTEX BREAKER

(71) Applicant: GE Healthcare Bio-Sciences AB, Uppsala (SE)

(72) Inventors: Klaus Heinrich Gebauer, Uppsala (SE); Rolf Axel Hjorth, Uppsala (SE); David Ronnholm, Marsta (SE)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 72 days.

(21) Appl. No.: 14/410,574

(22) PCT Filed: Jun. 20, 2013

(86) PCT No.: PCT/SE2013/050746
§ 371 (c)(1),
(2) Date: Dec. 23, 2014

(87) PCT Pub. No.: WO2014/003640
PCT Pub. Date: Jan. 3, 2014

(65) Prior Publication Data
US 2015/0125930 A1     May 7, 2015

(30) Foreign Application Priority Data
Jun. 26, 2012   (SE) ...................... 1250689

(51) Int. Cl.
*C12M 1/06*      (2006.01)
*C12M 1/00*      (2006.01)
*B01F 13/08*     (2006.01)
*B01F 15/00*     (2006.01)

(52) U.S. Cl.
CPC ............ *C12M 27/02* (2013.01); *B01F 13/08* (2013.01); *B01F 13/0827* (2013.01); *B01F 15/0085* (2013.01); *B01F 15/00896* (2013.01); *C12M 23/14* (2013.01); *C12M 23/26* (2013.01); *C12M 27/20* (2013.01); *B01F 2215/0073* (2013.01)

(58) Field of Classification Search
None
See application file for complete search history.

(56) References Cited

U.S. PATENT DOCUMENTS

| 3,570,819 | A | 3/1971 | Rosinger |
| 6,844,186 | B2 * | 1/2005 | Carll ................... B01F 11/0082 |
| | | | 366/243 |
| 2003/0227817 | A1 | 12/2003 | Martel et al. |
| 2012/0027324 | A1 * | 2/2012 | Morrissey ............... B01F 7/162 |
| | | | 383/105 |

FOREIGN PATENT DOCUMENTS

| DE | 451112 C | 10/1927 |
| JP | 09029084 A | 2/1997 |
| JP | 2002537868 A | 11/2002 |
| JP | 2004534544 A | 11/2004 |
| JP | 2007282629 A | 11/2007 |
| JP | 2010089151 A | 4/2010 |
| JP | 2011036189 A | 2/2011 |
| JP | 2014121302 A | 7/2014 |
| WO | 0053304 A1 | 9/2000 |
| WO | 2011102931 A2 | 8/2011 |
| WO | 2012015571 A1 | 2/2012 |

OTHER PUBLICATIONS

International Search Report issued in connection with corresponding WO application PCT/SE2013/050746 dated Sep. 20, 2013.
European Search Report dated Feb. 18, 2016 from the corresponding EP Patent Application No. 13810485.6.
Japanese Office Action Dated Mar. 14, 2017 From the Corresponding Japanese Application No. 2015-520118.

* cited by examiner

*Primary Examiner* — Suzanne M Noakes
*Assistant Examiner* — Stephen Chong
(74) *Attorney, Agent, or Firm* — Grogan, Tuccillo & Vanderleeden, LLP (57) ABSTRACT

A generally cylindrical collapsible mixing vessel, comprising: a) a flexible plastic film side wall, a top wall and a bottom wall, wherein both the top wall and the bottom wall are attached to the side wall and the side, top and bottom walls define an inner volume of the vessel; b) an agitator located in the inner volume and; c) at least one vortex breaker made from flexible plastic film, located in the inner volume and attached to the bottom wall and/or the side wall via string elements, wherein said vortex breaker extends along the side wall and inwards in a generally radial direction.

18 Claims, 8 Drawing Sheets

COLLAPSIBLE BAG WITH FLEXIBLE VORTEX BREAKER

CROSS-REFERENCE TO RELATED APPLICATIONS

This is a national stage application under 35 U.S.C. §371(c) of prior-filed, co-pending, PCT application serial number PCT/SE2013/050746, filed on Jun. 20, 2013, which claims priority to Swedish patent application serial number 1250689-5, filed on Jun. 26, 2012, the entire contents of which are incorporated by reference herein.

TECHNICAL FIELD OF THE INVENTION

Embodiments of the present invention relate to collapsible mixing vessels, and more particularly to vortex breakers for collapsible mixing vessels. Embodiments of the present invention also relate to a mixing unit with a collapsible mixing vessel mounted in a rigid support compartment and to a method of cultivating cells in a mixing unit.

BACKGROUND OF THE INVENTION

Single-use or disposable systems are rapidly increasing in biopharmaceutical industry due to the flexibility and cost-effectiveness of such systems. Disposable components in the systems are presterilized and qualified to regulatory requirements. Disposable systems are easy to adapt to different production purposes and it is easy and inexpensive to change a product line while good process reliability is at least maintained, if not even improved.

There are several kinds of mixing systems in which disposable containers or bags may be used. One type of such mixing system is a bioreactor in which cells or microorganisms can grow. Mixing systems are also used to prepare for example buffer and media. The mixing systems may comprise a support compartment which houses a disposable bag or container. The compartment may have a form of a cylinder, for example a substantially circular cylinder. The bag is placed inside the compartment in an accurate manner so that for example different pipelines, mixers and sensors can be connected to the bag properly and accurately. US2011/0310696 shows a mixing system of this kind For cell cultivation it is necessary to provide agitation in order to keep the cells suspended and to provide convective mass transport of nutrients, gases and metabolites. In larger bags, such as bags for use in support compartments, agitation is normally provided by a rotating agitator. To prevent vortexing it is then desirable to have one or more vortex breakers in the bag. WO2012/015571 describes a type of vortex breaker which is made from a sheet of plastic material extending from the bag walls across the bag. This arrangement has a drawback in that stagnant pockets are formed at the vortex breaker-bag wall interface, where cells and/or microcarriers with cells may accumulate. This applies in particular to pockets adjacent to the bottom wall of the bag. Accumulation of cells is undesirable as the cultivation conditions may deteriorate locally and signal substances released from the accumulated cells can affect the entire culture. Further, a vortex breaker extending horizontally across the bag as in WO2012/015571 will disturb the convective flow inside the bag.

Accordingly there is a need for a vortex breaker in collapsible vessels which does not form stagnant pockets and which enables a good convective flow.

SUMMARY OF THE INVENTION

One aspect of the invention is to provide a collapsible mixing vessel free from stagnant pockets. This is achieved with a vessel as defined in claim 1.

One advantage is that a good convective flow pattern without stagnant zones can be obtained. Further advantages are that the vortex breaker is flexible and can be collapsed with the mixing vessel, yet allows for tensioning to withstand the viscous drag forces when in use.

A second aspect of the invention is to provide a mixing unit comprising a collapsible mixing vessel mounted in a rigid support compartment. This is achieved with a unit as defined in the claims.

A third aspect of the invention is to provide a stagnant zone-free method for cell cultivation in a mixing unit. This is achieved with a method as defined in the claims.

Further suitable embodiments of the invention are described in the dependent claims.

DETAILED DESCRIPTION OF EMBODIMENTS

In one aspect the present invention discloses a generally cylindrical collapsible mixing vessel 1;11;21;31;41;51;81 which comprises:

a) a flexible plastic film side wall 3;13;23;33;43;53;73, a top wall 2;12;22;32;42;52;72 and a bottom wall 4;14;24;34; 44;54;74, wherein both the top wall and the bottom wall are attached to the side wall and the side, top and bottom walls together define an inner volume 5;15;25;35;45;55;75 of the vessel;

b) an agitator 6;16;26;36;46;76 located in the inner volume and;

c) at least one vortex breaker 7;17;27;37;47;57;77 made from flexible plastic film. The vortex breaker or vortex breakers is/are located in the inner volume of the vessel and is/are attached to the bottom wall and/or the side wall via string elements 8;18;28;38;48;49;58;78;79 and extend(s) along the side wall and inwards in a generally radial direction. The directions top, bottom, along and inwards here refer to when the vessel is in the extended (non-collapsed) state and ready for use. One or more of the bottom and the top wall may be rigid, but they may also be flexible, in which case the vessel can be defined as a bag. The shape of the vessel may be cylindrical with a circular cross section and circular top and bottom walls. The bottom wall may be flat, or it may be tapered, e.g. in a rounded or frustoconical shape.

In cases where the transition between the side wall and the top or bottom wall is gradual, the part where (in use) the angle between the wall and the vertical axis is less than 45 degrees is defined as the side wall. The vessel can comprise one vortex breaker or a plurality of vortex breakers, such as at least two, three or four. The vortex breakers can e.g. extend vertically and be regularly spaced around the perimeter of the vessel. They can also be acutely angled relative to the vertical axis. The vortex breakers can be made from single ply plastic film or from a multilayer laminate. Their length can be such that when the vessel is filled with liquid and inflated, they are somewhat tightened. The string elements can e.g. be monofilaments of plastics, elastomers or metals, or they can be multifilament yarns. They can also comprise tubular elements. The string elements can e.g. be attached by welding to the vessel walls and/or vortex breakers, or via fasteners located on the vessel walls and/or vortex breakers. The fasteners can be e.g. in the form of hooks, loops, clamps etc. and the string elements can be attached to them e.g. by clamping, knotting or by passing a loop through the fastener. The agitator may be arranged for rotational agitation and can be located at the bottom end of the vessel, e.g. as described in WO2003028869. Alternatively, the agitator can be suspended from the top wall of the vessel (see e.g U.S. Pat. Nos. 4,355,906 and 7,547,135) or mounted on a shaft attached to both the top and bottom walls as in WO2009143925. The vessel may further comprise a plurality of ports for transport of culture media, cell inoculates, nutrients, gases, perfusion streams, sampling etc. and it may also comprise ports/windows for sensors. The ports may be equipped with sanitary connectors, e.g. Ready-Mate™ aseptic connectors from GE Healthcare. The collapsible mixing vessel can be disposable and be designed for use in a re-usable rigid support compartment. It can be used for cell cultivation, but also for preparation of cell culture media, buffer preparation etc. in the bioprocess industry. It can also be used in other areas where mixing of liquids under hygienic conditions is needed, e.g. in medical applications or in dairy or beverage industries.

Attachment to the bottom wall via string elements means that the vortex breaker(s) is/are attached to the bottom of the vessel, where the need for a vortex breaker is highest, but due to the string elements a gap is formed between the bottom wall and the vortex breaker, such that no stagnant zones are formed. The gap between the vortex breaker(s) and the bottom wall of the vessel may e.g. be at least 5 mm or 1 cm, such as 1-20 cm or 1-10 cm. The string elements are narrow, such as with a diameter or largest cross-section dimension of less than 5 mm or less than 2 mm, which is too small for the formation of stagnant zones around their attachment points. The vortex breaker(s) can also be attached to the side wall (e.g. opposite parts of the side wall) via string elements, which allows for the formation of a gap between the vortex breaker and the side wall. With this arrangement it is also possible to have a gap between the vortex breaker(s) and the bottom wall of the vessel as described above. The vortex breaker(s) can be arranged such that they do not extend into the central part of the vessel, such as the volume within half a radius from the center axis of a circular cylindrical vessel. This improves the convective circulation in the vessel.

In some embodiments, vortex breaker(s) is/are also attached to the top wall, such as via string elements 9;29; 39;59. In use, the mixing vessel will only be partially filled with liquid, e.g. up to 80% of the bag volume. Hence there will not be any liquid at the top of the vessel and if desired, the vortex breaker(s) can be directly attached, e.g. welded, to the top wall without any stagnant zone issues. They may however equally well be attached via string elements 9;29; 39;59 also to the top wall. In certain embodiments, the only attachment of the vortex breaker(s) to the walls of the vessel (i.e. the top wall, the bottom wall or the side wall) is via string elements.

In some embodiments, illustrated by FIGS. 4-7, at least one string element 38,39; 48,49;58,59;78, such as at least one or two string elements for each vortex breaker 37;47; 57;77, is/are attached to both the bottom wall and the top wall or to opposing segments of the side wall. This has the advantage that the string elements can take up the tension load on the vortex breakers. The string elements can e.g. be joined to one or both of the edges of each vortex breaker.

Figure 1:
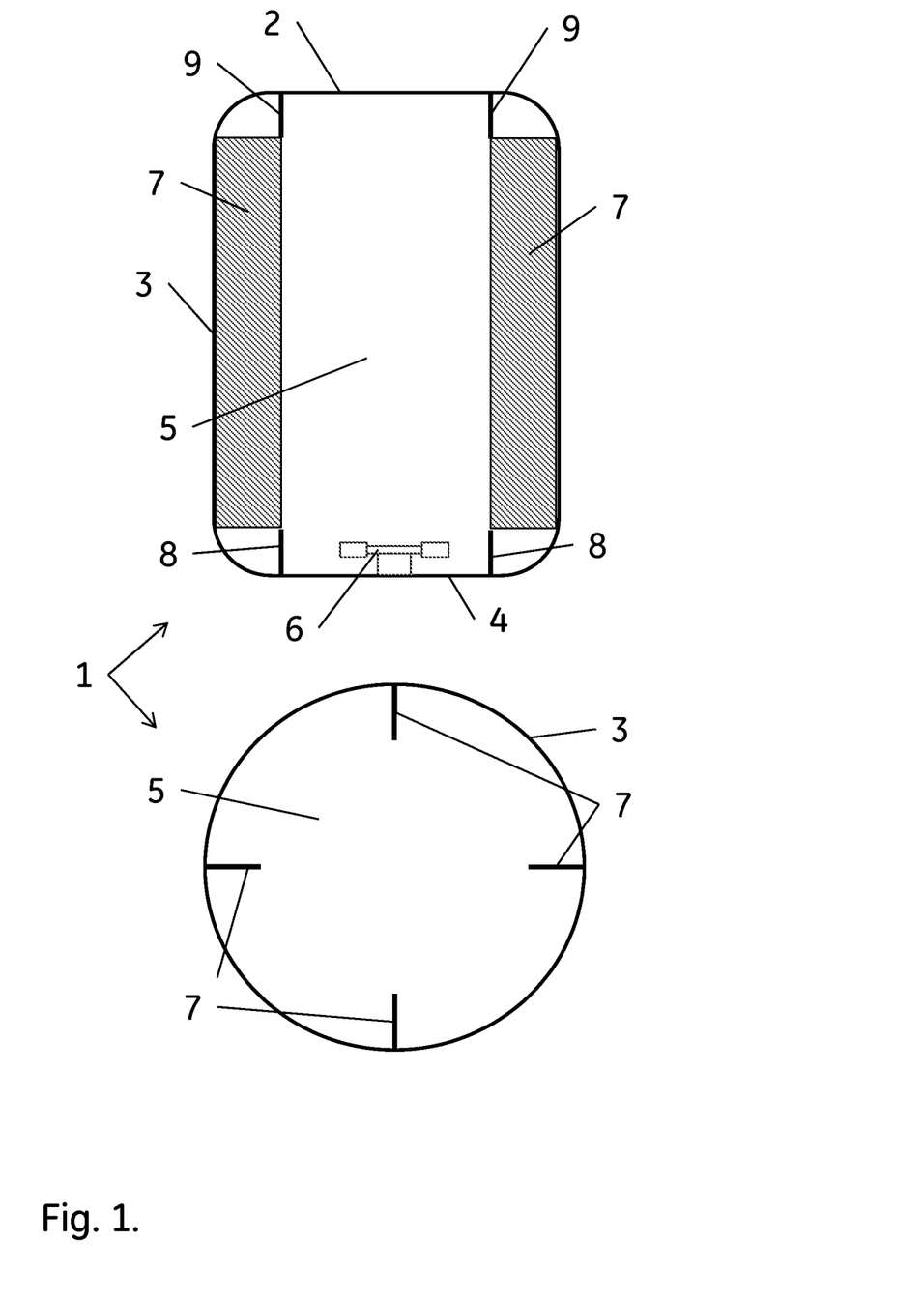
FIG. 1 shows a mixing vessel with four vortex breakers according to an embodiment of the invention.
Figure 2:
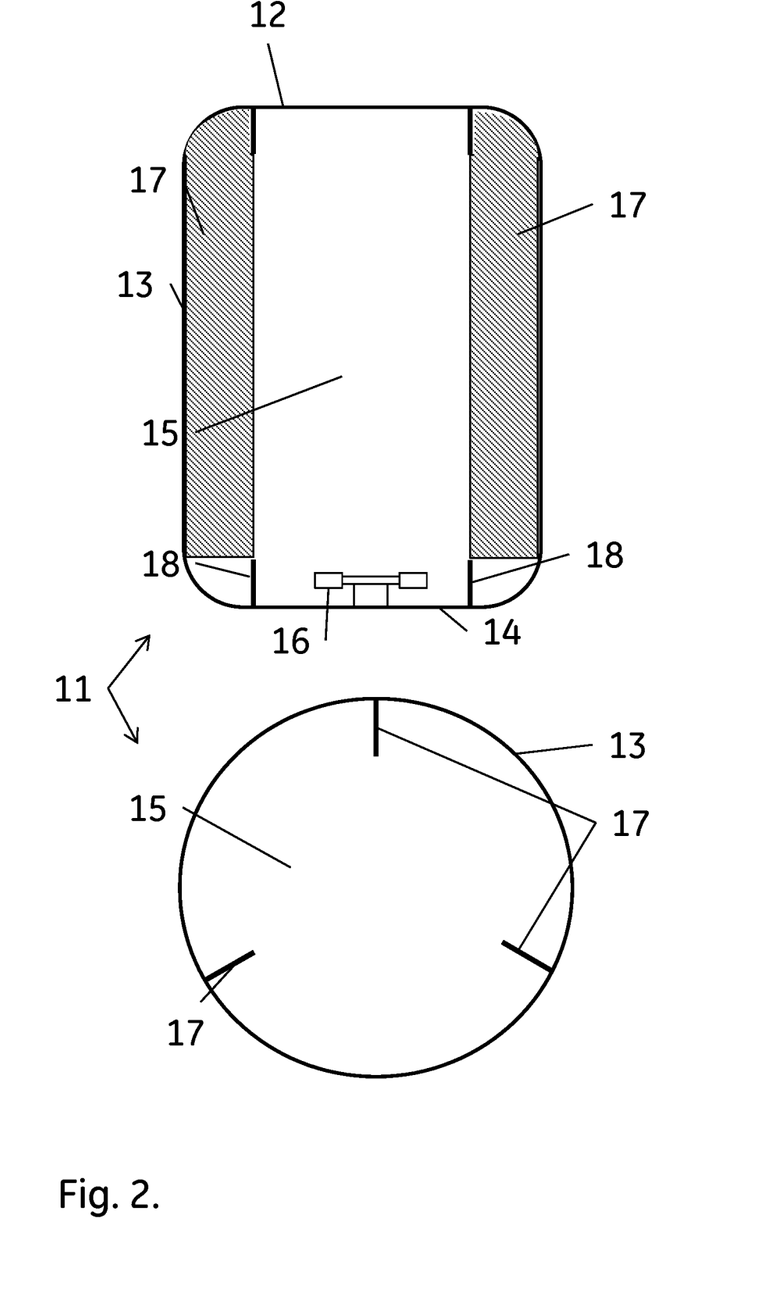
FIG. 2 shows a mixing vessel with three vortex breakers according to an embodiment of the invention.
Figure 3:
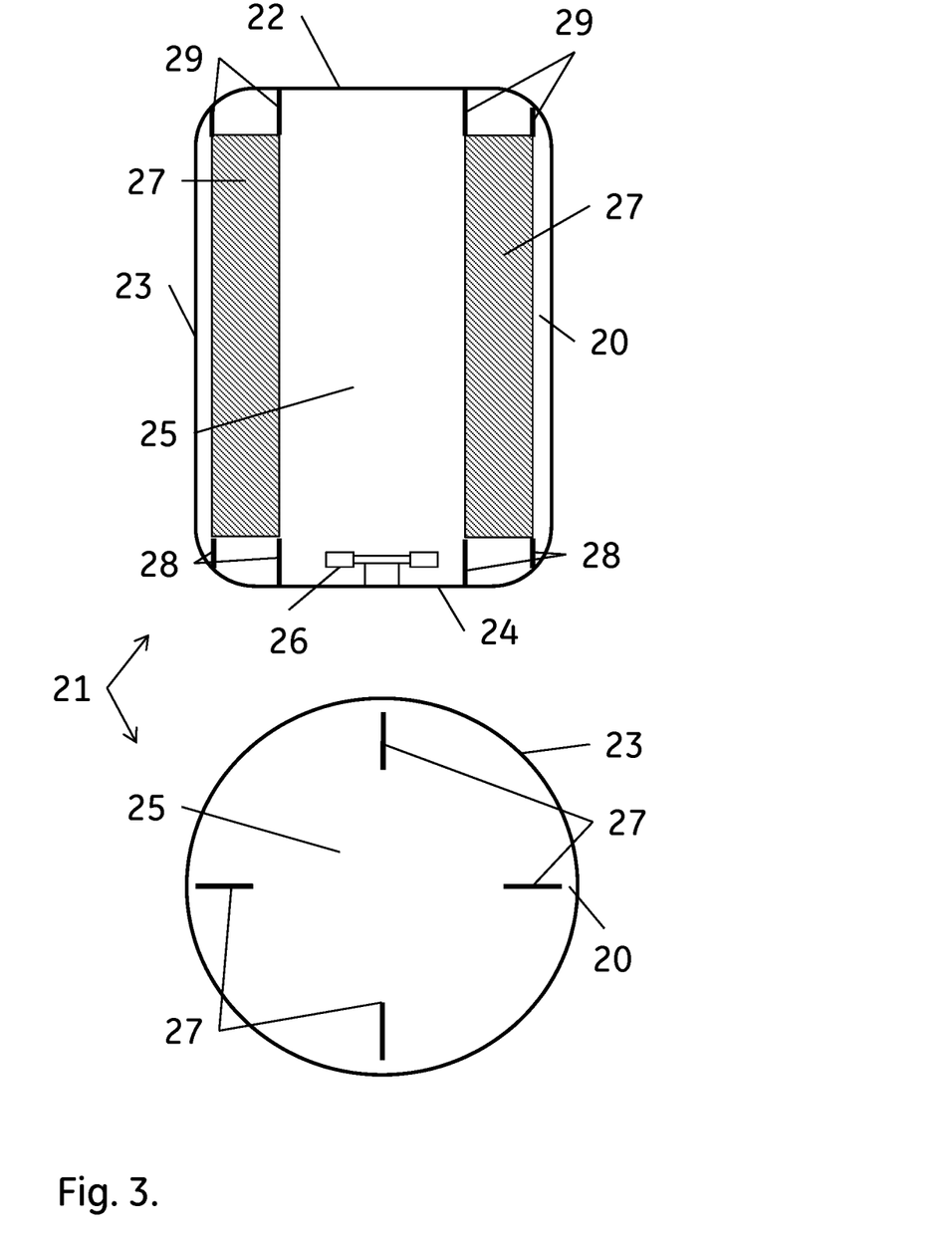
FIG. 3 shows a mixing vessel with four vortex breakers according to an embodiment of the invention.
Figure 4:
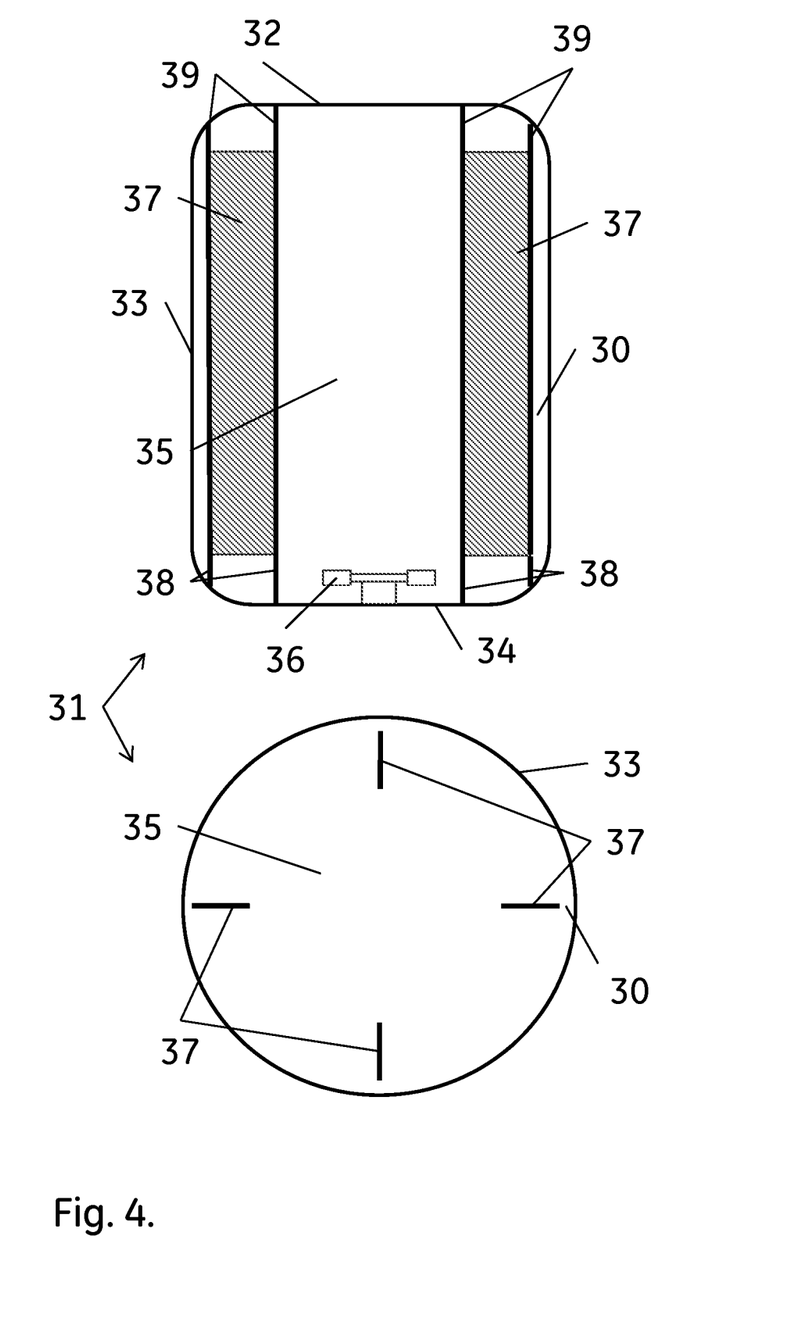
FIG. 4 shows a mixing vessel with four vortex breakers according to an embodiment of the invention.
Figure 5:
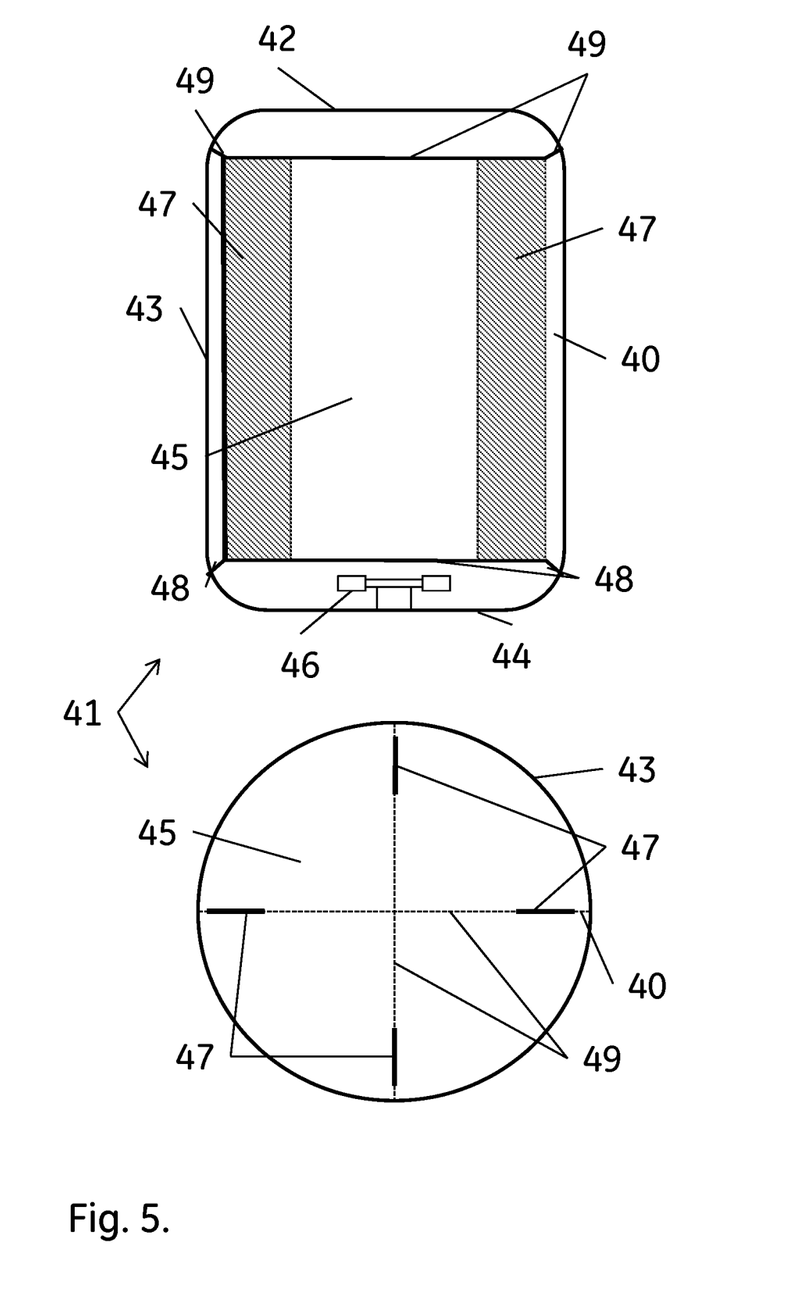
FIG. 5 shows a mixing vessel with four vortex breakers according to an embodiment of the invention.
Figure 6:
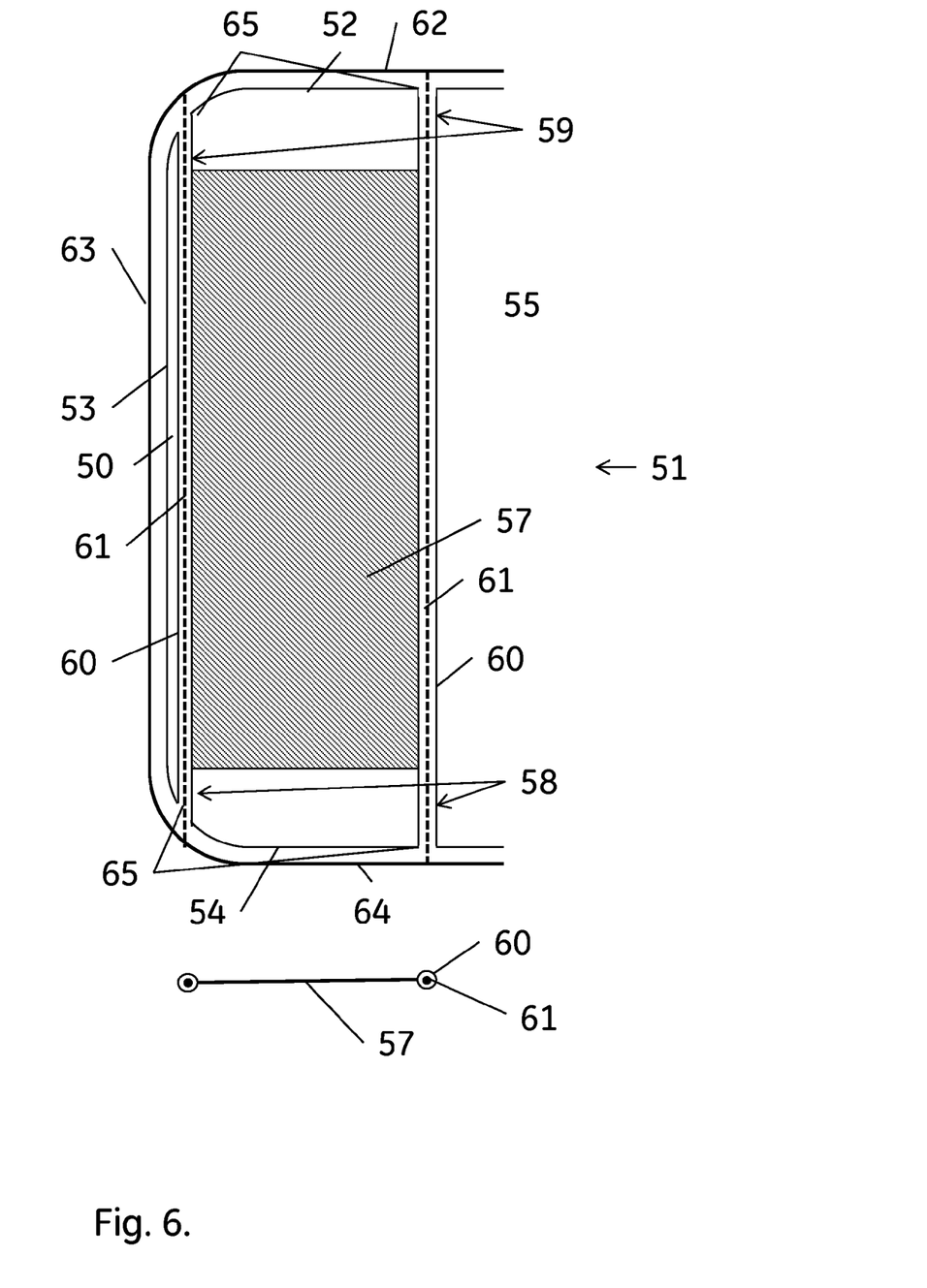
FIG. 6 shows an enlarged view of a vortex breaker with tubular string elements according to an embodiment of the invention.
Figure 7:
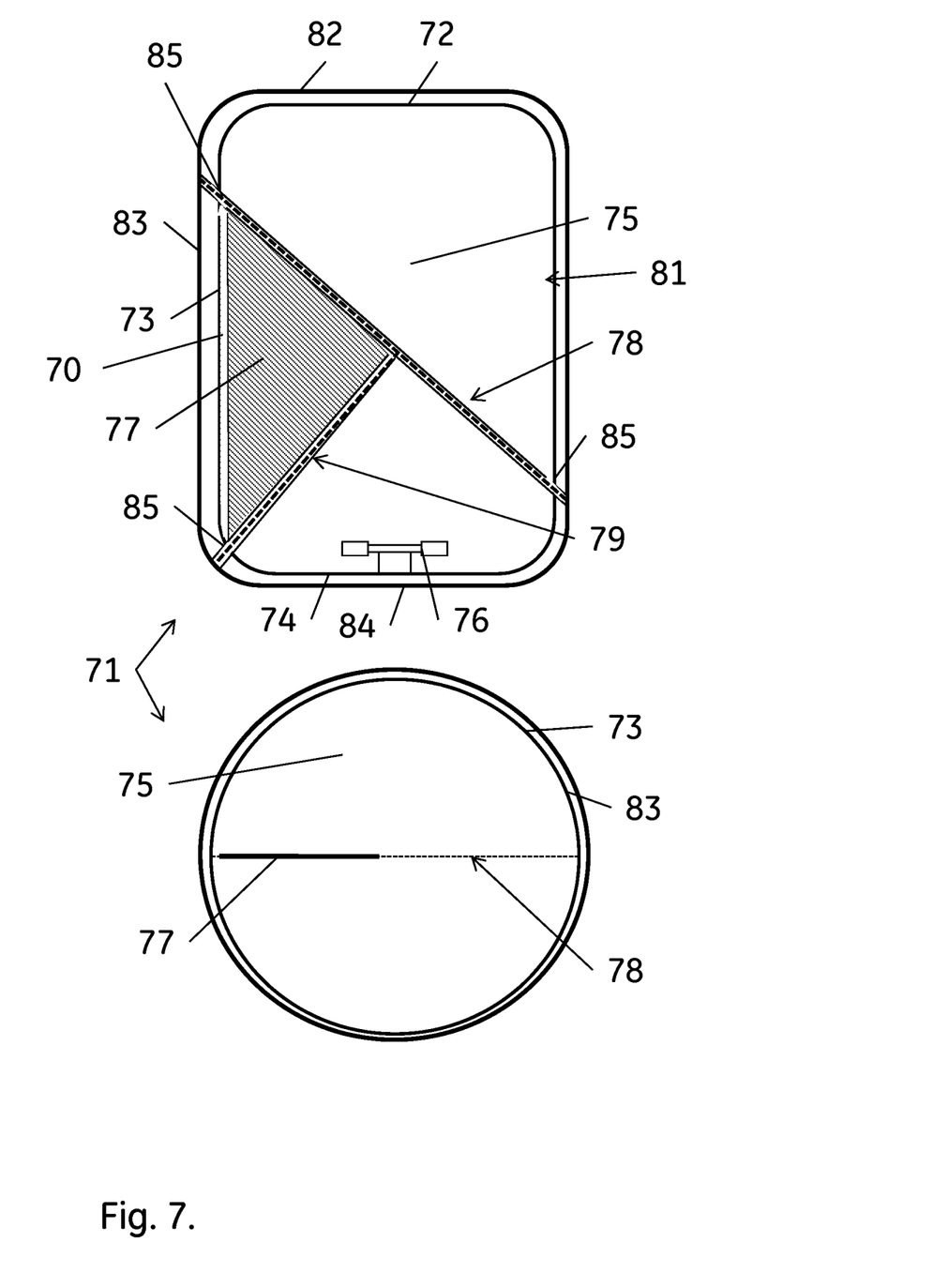
FIG. 7 shows a mixing vessel and a mixing unit according to an embodiment of the invention, with one vortex breaker.

In certain embodiments, illustrated by FIGS. 6 and 7, the string elements 58;59;78;79 comprise tubing 60 and a wire 61 inside the tubing. At least one string element can e.g. comprise a) tubing 60 attached to the vortex breaker, e.g. along the edge(s) of the vortex breaker(s) and via tubular ports 65;85 to the top 52 and bottom 54;74 walls or to opposing segments of the side wall 73 of said collapsible mixing vessel and b) a wire 61 passing through said tubing and tubular ports and arranged for being attached to either a top 62 and a bottom 64;84 wall of a rigid support compartment arranged for accommodating said collapsible mixing vessel or to opposing segments of the side wall 83 of said support compartment. The tubing can e.g. be welded to the edge(s) of each vortex breaker and the wire(s) can be present in the tubing at delivery of the vessel, but they can also be introduced in the tubing during mounting of the collapsible vessel in a rigid support compartment. The tubing ports in the vessel walls should be located in locations corresponding to wire attachment points on the compartment walls. The wires will not come into contact with the inner volume of the vessel, so they do not have to be sterile. The wires can be thin metal wires, but they can also be made from polymeric materials such as polyester, polyamides etc. An advantage of the wire-in-tube arrangement is that the collapsible vessel walls do not need to carry the tensioning load, which can be convenient, particularly when all the walls of the vessel are flexible.

In some embodiments, illustrated by FIGS. 3-8, a gap 20; 30;40;50;70 of at least 2 mm, such as 2-50 mm or 5-50 mm, is formed between each vortex breaker 27;37;47;57;77 and the side wall 23;33;43;53;73. This again refers to when the vessel is in the extended (non-collapsed) state and ready for use. The gap ensures that no stagnant zones are formed.

In certain embodiments, the agitator 26;36;46;76 is arranged to be magnetically driven and hermetically enclosed in the vessel to ensure sterility. It can e.g. be prepared from a radiation-stable plastic, incorporate a magnet and be designed to levitate or to rotate around a slide bearing. It can e.g. be located at the bottom of the bag, adjacent a magnetic drive outside the bag on the bottom wall of a rigid support compartment. The agitator may carry different impeller designs depending on its specific use such as low shear or high rpm mixing, e.g. turbines, propellers and other designs known in the art.

In some embodiments, the collapsible mixing vessel has been sterilized, such as by gamma or electron beam irradiation. Sterility is needed for cell cultivation and it is convenient to sterilize by subjecting the mixing vessel, including the vortex breaker(s) and the agitator, to ionizing radiation, such as gamma or electron beam irradiation. It is advantageous if the materials of construction in all irradiated components are sufficiently radiation-stable that deterioration in mechanical properties and/or formation of leachables after irradiation is avoided or minimized. Suitable materials can be polyethylene, ethylene copolymers, polyamide etc.

Figure 8:
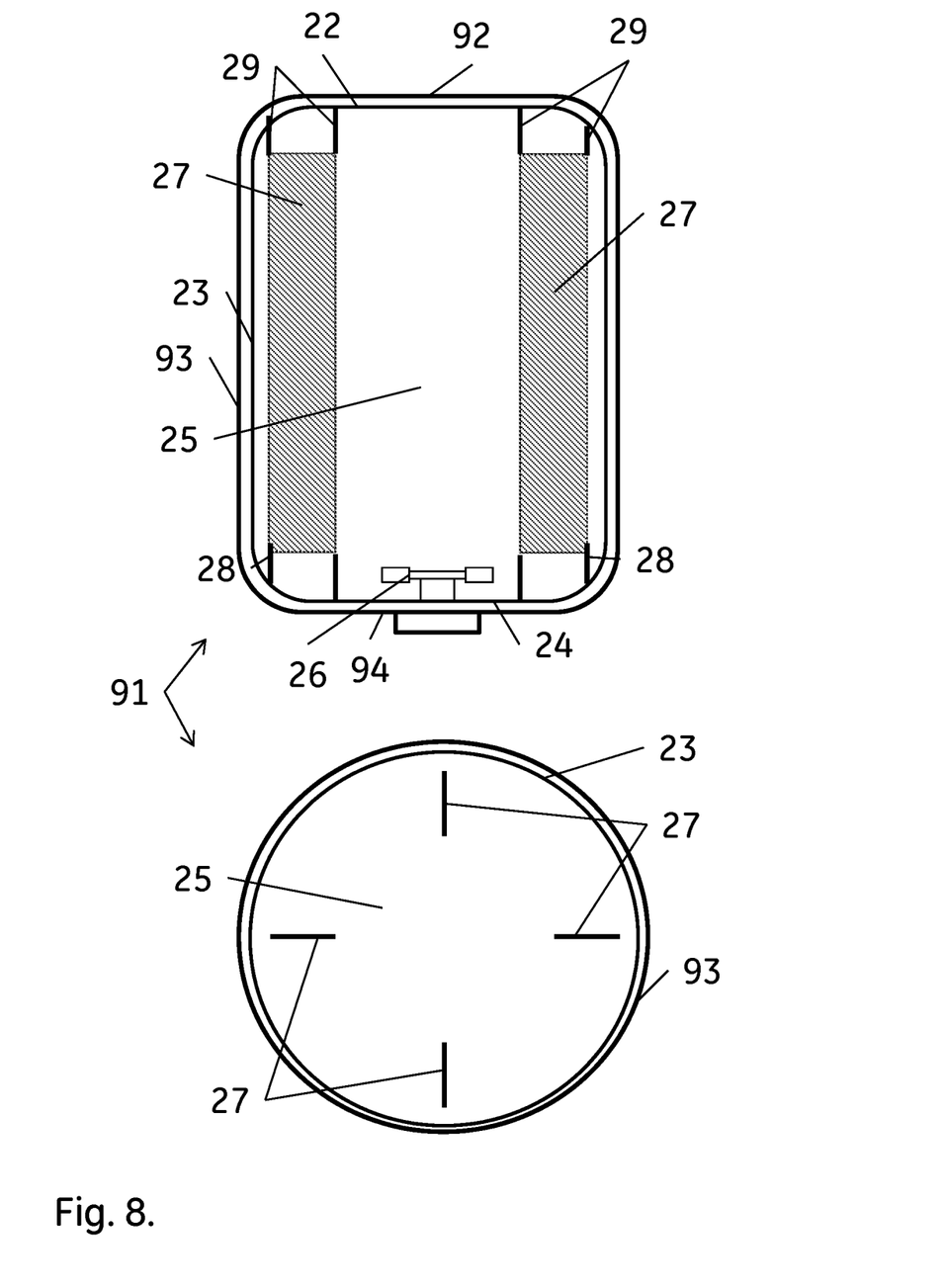
FIG. 8 shows a mixing vessel and a mixing unit according to an embodiment of the invention.

In a second aspect, illustrated by FIGS. 6-8, the present invention discloses a mixing unit 71;91 comprising the mixing vessel as described in any of the above embodiments, mounted in a rigid support compartment, which can e.g. be manufactured from stainless steel or other metals. The support compartment is designed to carry the load of the liquid inside the flexible mixing vessel and the mixing vessel and the support compartment can be co-designed to give a snug fit of the vessel inside the compartment. The support compartment may e.g. be cylindrical with a circular cross section. An example of a rigid support compartment suitable for use in an embodiment of the invention is the XDR™ bioreactor system available from Xcellerex, Inc. USA.

In some embodiments, illustrated by FIGS. 6 and 7, at least one, such as two, string elements 58;59;78;79 for each vortex breaker comprise a) tubing 60 attached to the vortex breaker and via tubular ports 65;85 to the top 52 and bottom 54;74 walls or to opposing segments of the side wall 73 of said collapsible mixing vessel and b) a wire 61, such as a metal wire, passing through said tubing and tubular ports and attached to a top 62 and a bottom 64;84 wall of the rigid support compartment or to opposing segments of the side wall 83 of said compartment. The arrangement of the tubing and the wires can be as described above and the wires may be attached to the support compartment by different fastening and tensioning means, e.g. screw or excenter fittings.

In certain embodiments the mixing unit further comprises a cell culture medium, cells and optionally microcarriers in the inner volume of the collapsible mixing vessel. This allows cell cultivation to be performed in the mixing vessel.

In a third aspect the present invention discloses a method for cell cultivation comprising the steps of:

a) providing a mixing unit according to any one of the embodiments described above;

b) partially filling the collapsible mixing vessel with cell culture medium and optionally microcarriers;

c) adding cells, such as a cell inoculate, to the cell culture medium and;

d) cultivating the cells under agitation provided by the agitator.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Features from different aspects and embodiments may be combined to form new embodiments.

The invention claimed is:

1. A generally cylindrical collapsible mixing vessel, comprising:
a flexible plastic film side wall, a top wall and a bottom wall, wherein both the top wall and the bottom wall are attached to the side wall and the side, top and bottom walls define an inner volume of the vessel;
an agitator located in the inner volume; and
at least one vortex breaker made from flexible plastic film, located in the inner volume and attached to the bottom wall and/ or the side wall via string elements, wherein said vortex breaker extends along the side wall and inwards in a generally radial direction;
wherein a largest cross-sectional dimension of each of the string elements is less than approximately 5 mm.

2. The mixing vessel according to claim 1, with a gap of at least 5 mm between each vortex breaker and the bottom wall.

3. The mixing vessel according to claim 1, wherein said at least one vortex breaker is attached to the top wall.

4. The mixing vessel according to claim 1, wherein said at least one vortex breaker is only attached to the walls of the vessel via string elements.

5. The mixing vessel according to claim 1, wherein at least one string element for each vortex breaker is attached to both the bottom wall and the top wall or to opposing segments of the side wall.

6. A generally cylindrical collapsible mixing vessel, comprising:
a flexible plastic film side wall, a top wall and a bottom wall, wherein both the top wall and the bottom wall are attached to the side wall and the side, top and bottom walls define an inner volume of the vessel;
an agitator located in the inner volume; and
at least one vortex breaker made from flexible plastic film, located in the inner volume and attached to the bottom wall and/ or the side wall via string elements, wherein said vortex breaker extends along the side wall and inwards in a generally radial direction;
wherein at least one string element for each vortex breaker is attached to both the bottom wall and the top wall or to opposing segments of the side wall;
wherein said at least one string element comprises:
tubing attached to the vortex breaker and via tubular ports to the top and bottom walls or to opposing segments of the side wall of said collapsible mixing vessel; and
a wire passing through said tubing and tubular ports and arranged for being attached to a top and a bottom wall or to opposing segments of the side wall of a rigid support compartment arranged for accommodating said collapsible mixing vessel.

7. The mixing vessel according to claim 1, further comprising a gap of at least 2 mm between each vortex breaker and the side wall.

8. The mixing vessel according to claim 1, wherein the agitator is arranged to be magnetically driven.

9. The mixing vessel according to claim 1, which has been sterilized.

10. The mixing vessel according to claim 1, with a gap of at least 1 cm between each vortex breaker and the bottom wall.

11. The mixing vessel according to claim 1, with a gap of 1 cm to 10 cm between each vortex breaker and the bottom wall.

12. The mixing vessel according to claim 1, wherein said at least one vortex breaker is attached to the top wall via string elements.

13. The mixing vessel according to claim 1, further comprising a gap of 2 mm to 50 mm between each vortex breaker and the side wall.

14. The mixing vessel according to claim 1, which has been sterilized by gamma or electron beam irradiation.

15. The mixing vessel according to claim 1, wherein the largest cross-sectional dimension of each of the string elements is less than approximately 2 mm.

16. The mixing vessel according to claim 1, wherein the string elements provide an indirect connection between the vortex breaker and at least one of the bottom wall, top wall and side walls of the vessel.

17. The mixing vessel according to claim 1, wherein the vortex breaker does not extend into a volume within approximately half a radius from a center axis of the vessel.

18. The mixing vessel according to claim 1, wherein the vortex break is only attached to the top wall, bottom wall or side wall by the string elements.

* * * * *

UNITED STATES PATENT AND TRADEMARK OFFICE
CERTIFICATE OF CORRECTION

PATENT NO. : 9,663,752 B2
APPLICATION NO. : 14/410574
DATED : May 30, 2017
INVENTOR(S) : Klaus Heinrich Gebauer et al.

It is certified that error appears in the above-identified patent and that said Letters Patent is hereby corrected as shown below:

On the Title Page

The Assignee section should read --GE Healthcare Bio-Sciences AB, Uppsala, Sweden--

Signed and Sealed this
First Day of August, 2017

Joseph Matal
*Performing the Functions and Duties of the*
*Under Secretary of Commerce for Intellectual Property and*
*Director of the United States Patent and Trademark Office*